United States Patent [19]

Meller

[11] Patent Number: 4,642,738
[45] Date of Patent: Feb. 10, 1987

[54] ILLUMINATED DENTAL DRILL

[76] Inventor: Moshe Meller, 20 Rachel Street, Haifa, Israel, 34402

[21] Appl. No.: 819,871

[22] Filed: Jan. 16, 1986

[30] Foreign Application Priority Data

Feb. 21, 1985 [IL] Israel ......................... 74405

[51] Int. Cl.$^4$ ........................... A61C 1/00; A61C 3/00
[52] U.S. Cl. ..................................... 362/119; 433/29; 433/114
[58] Field of Search ............... 362/119, 120, 302, 171, 362/172, 178, 208, 375; 433/29, 114, 133

[56] References Cited

U.S. PATENT DOCUMENTS

| | | | |
|---|---|---|---|
| 2,226,616 | 12/1940 | Kraus | 362/119 |
| 2,588,288 | 3/1952 | Dobanka | 362/119 |
| 2,588,559 | 3/1952 | Needham | 362/120 |
| 2,673,284 | 3/1954 | Henderson | 362/120 |
| 2,885,537 | 5/1959 | Wood, Jr. | 362/119 |
| 3,023,306 | 2/1962 | Kesdor | 362/119 |
| 3,109,238 | 11/1963 | Marks | 32/27 |
| 3,614,414 | 10/1971 | Gores | 362/119 |
| 4,107,765 | 8/1978 | Singadon et al. | 362/119 |
| 4,184,196 | 1/1980 | Moret et al. | 433/29 |
| 4,195,329 | 3/1980 | Woog | 362/120 |
| 4,230,453 | 10/1980 | Reimers | 362/119 |
| 4,283,757 | 8/1981 | Nahbandian et al. | 362/119 |
| 4,375,964 | 3/1983 | Knopp | 433/29 |
| 4,561,845 | 12/1985 | Meller | 433/29 |

Primary Examiner—Raymond A. Nelli
Attorney, Agent, or Firm—Frishauf, Holtz, Goodman & Woodward

[57] ABSTRACT

A pneumatic dental drill handpiece has a light-bulb (40) fastened in its head, so directed that it illuminates the tip of the burr (32). An electric cell (2) is positioned in a semicylindrical chamber (15) located in the rear part (10) of the handpiece casing; the chamber is eccentric to the axis of the casing and is accessible through an opening therein, this opening being closed by a thin sleeve (9) slidable on the rear part. Ducts for admission of air (13) and water (12) extend through a channel (17) in the portion of the casing opposite the opening. Electric contact between the front pole of the cell (2) and one terminal of the bulb (40) is made by a conductor wire (21) passing through the hollow front part (20), and between the rear pole of the cell and the second terminal of the bulb through the anodized aluminum parts (10) and (20) of the casing. The aluminum parts are conductively connected through non-anodized contacting surfaces.

11 Claims, 2 Drawing Figures

ILLUMINATED DENTAL DRILL

BACKGROUND OF THE INVENTION

The invention relates to dental drills, more especially to means for direct illumination of the area in the mouth which is being worked on.

Dental work on teeth and other parts of the oral cavity has to be very accurate and delicate and, therefore, requires a high light intensity beamed onto the area worked upon. The dental surgeon who works in an otherwise dark cavity must be able to direct a strong light beam onto the spot which he drills or grinds, which should not be obstructed by the shadow of his hands or his head.

With primitive equipment this is still the case whereby the dentist has to direct the light rays from an external light source into the mouth by means of a small mirror. This method is highly inconvenient, since it occupies both hands, one hand holding the drilling or grinding tool and the other hand holding the mirror, in addition to the danger of the light-ray between source and mirror being obscured by the hands or the body of the dental surgeon.

For this reason direct illumination was introduced a few years ago, the method comprising the use of optical fibres for transferring a light beam from an external static source to a point just above the drill point or burr inserted into the tool. The light source is generally situated at the central control post whence the light beam is directed into the receiving end of a resilient optical fibre. A first optical fibre extends from the light source as far as the standard connector guided through the rubber hose, at which point it is transferred to a second optical fibre by means of a special connector; the second fibre runs inside the drill along the turbine housing and ends in the drill head while pointing towards the drill point.

Instead of being hampered by these external optical connections to the handpiece in addition to the unavoidable water and air connections, it was found more efficient to locate the energy source inside the handpiece proper; with this object in view I have designed different embodiments of high-speed and low-speed drills, incorporating either a light generator or an electric cell of adequate output.

Israeli Patent Application No. 67784 (corresponding to U.S. Pat. No. 4,561,845) I have disclosed a dental high-speed handpiece which comprises illuminating means in the form of a light bulb attached to its front end so directed as to illuminate the tip of the burr, an electric cell enclosed in the handpiece casing, and wiring connecting the bulb to the cell. The electric cell is enclosed in a centrally positioned chamber in the rear portion of the casing which can be opened, for the purpose of exchanging the electric cell, by removing a cylindrical plug normally inserted into the rear opening of the chamber. This plug contains connectors to the external air and water lines as well as the respective air and water ducts, and carries an electrical contact point urged toward the rear end of the cell. Air and water ducts extend from the ends of the corresponding ducts inside the plug to the front end of the handpiece while running close to the outside wall of the casing, in order to leave room for the chamber containing the cell. Wiring between the cell terminals and the light bulb are, for most of the way, enclosed in the air ducts which serve to supply compressed air to the turbine wheel of the drill and to return exhaust air to the rear of the handpiece.

An improvement of this dental drill is described in Israeli Patent Application No. 69062. Herein a low-speed drill operated by an air motor is provided with illuminating means similar to those incorporated in the handpiece of the high-speed drill. The improvement consists in replacing the electric wiring by the parts of the aluminum casing which are anodized all over, except in those places which should serve for transmitting electric current from one component to another. In this embodiment the ducts carrying air to the air motor, and water to the drill head run along the outer wall of the casing so as to leave sufficient space for the centrally positioned electric cell and air motor.

Both embodiments have proved to be very efficient and suitable for dental drilling, however they still suffer from certain drawbacks which to overcome is the object of the present invention:

1. Each of the aforedescribed handpieces is provided with an electric switch serving to connect the light bulb to the cell as soon as drilling operations are started. This requires additional action of the dental surgeon, it complicates the design and adds to the overall cost of the dental drill.

2. The plug closing the electric cell chamber and carrying the air and water ducts, besides of containing the contact piece to the rear terminal of the cell, is necessarily sealed by gaskets or O-rings from the rest of the casing, in order to prevent water from entering the cell chamber and from short-circuiting the illumination circuit. Replacement of the electric cell by removal and reinsertion of the plug requires a relatively expensive system of coordinating the ducts inside the plug and inside the casing, which adds to the difficulties in preventing water from leaking into the cell chamber.

SUMMARY OF THE INVENTION

With a view to overcoming these drawbacks, the present invention consists of a handpiece comprising an eccentrically positioned chamber for an electric cell which permits access from the side instead from the back of the casing, and which can be readily covered by a slidingly movable metal sleeve.

Another new feature of the improved handpiece is an automatic switch effecting communication between the electric cell and the light bulb in the front end, by being operated by air pressure as soon as air is admitted to the turbine wheel rotating the drill burr.

As in Israeli Application No. 69062, the anodized metal parts of the casing form electric conduits between the cell and the light source, with the difference that the sliding switch near the front end—provided to the previous embodiment—has been abolished and replaced by the automatic air-operated switch.

Owing to the eccentric placement of the electric cell, there remains sufficient space for water- and air-ducts along the casing side not occupied by the cell chamber, these ducts being either in the form of tubes or being incorporated in the material of the casing wall. A cover is provided close to the head of the handpiece enclosing the turbine wheel, permitting ready exchange of the light bulb.

The automatic switch is in the shape of a contact piston positioned in the rear part of the casing, with its rear end exposed to pressure of air admitted to the handpiece. The piston is urged to the rear against the air pressure by a helical spring which is designed to be compressed by pressure commonly employed with high-speed drills, and after compression of the spring it contacts the piston the rear terminal of the electric cell. The piston is conductively connected to the casing which is adapted to transmit the current to one terminal of the lightbulb. The front terminal of the cell is pressed onto a contact point at a front end of the cell chamber by the force of the contact piston which, in its turn, is urged onto the rear end of the cell by air pressure. The said contact point is conductively connected to the second terminal of the light bulb, whenever the electric circuit is closed by the above contact piston.

DESCRIPTION OF A PREFERRED EMBODIMENT

Figure 1:
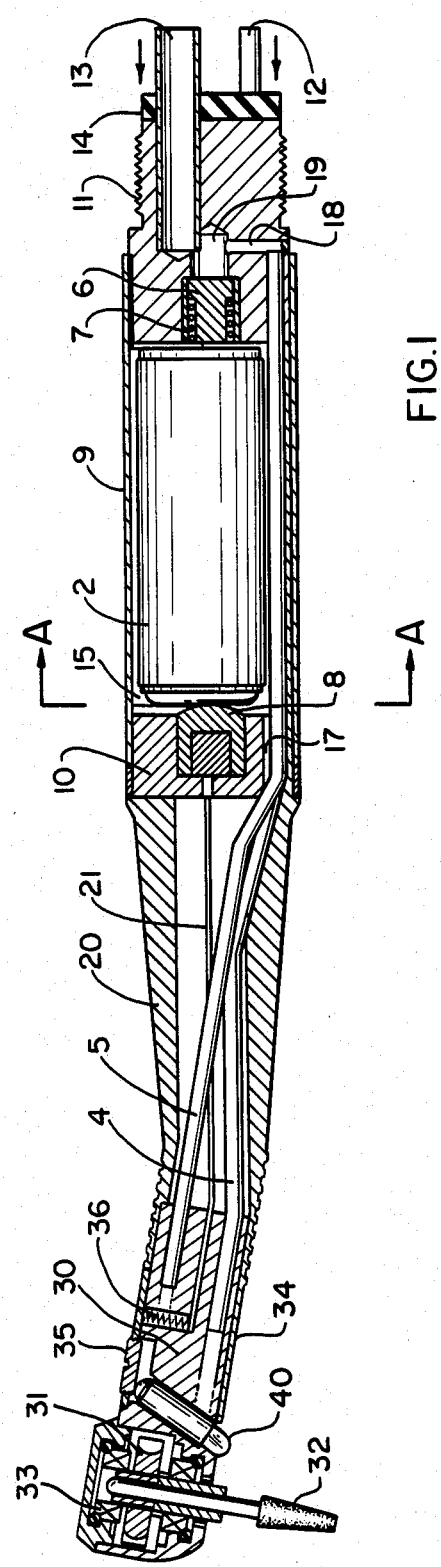
FIG. 1 is a longitudinal section through a high-speed drill handpiece, showing in particular the illuminating means.
Figure 2:
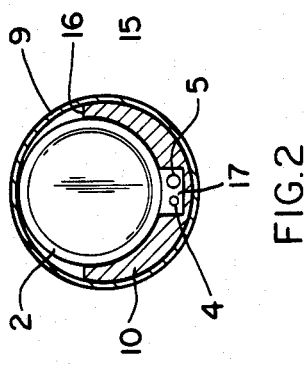
FIG. 2 is a section along the line A—A of FIG. 1.

In accordance with the drawing a high-speed drill handpiece comprises an aluminum casing which, for the sake of ready manufacture, is composed of three parts: a substantially cylindrical rear part 10, a crooked intermediate part 20, and a frontally inserted part 30. The rear part is provided with screw thread 11 for connecting it to a screw-threaded socket at the end of a flexible hose carrying water and air tubes in a conventional manner. A water inlet pipe 12 and an air inlet pipe 13 enter the flat rear end of the rear part, while a gasket 14 serves to seal it in the socket. The rear part contains a semi-cylindrical chamber 15 which is eccentrically positioned in respect to the axis of the casing, the latter being cut off (16) along the sides of the chamber, so as to permit ready insertion therein of an electric cell 2. The portion of the casing part opposite the open portion is recessed to form a longitudinal channel 17 serving to accommodate a water duct 4 and an air duct 5 which communicate at their rear ends with the water inlet 12 and the air inlet 13 respectively. Communication between the air duct 5 and the inlet 13 is via a transverse bore 18 and a central cylindrical bore 19, which opens into the chamber 15. The bore 19 contains a stepped contact piston 6 movable in axial direction and urged towards the rear by a helical spring 7. The front end of the rear casing part contains a similar central bore which contains a contact piece 8 firmly positioned therein and contacting the front terminal of the electric cell 2. A metal sleeve 9 is slidingly mounted on the cylindrical surface of the rear part and is adapted to be slid off this portion for the purpose of exposing the chamber 15 while exchanging the electric cell 2. When slid back, the sleeve 9 covers the chamber—as shown in the drawing—and protects the cell against penetration of humidity.

The intermediate part 20 is hollow and contains the front part 30 which is firmly inserted into the cylindrical front end of the part 20. The air- and water-ducts 4 and 5 extend through the hollow portion and enter suitable bores provided in the front part. In addition, an insulated conductor wire 21 extends through the hollow portion and connects the contact piece 8 with the front part 30.

The front part 30 comprises a cylindrical rear portion which is firmly inserted into the intermediate part and a drill head comprising, in a conventional manner, a turbine wheel 31 which drives a burr 32 and is carried in bearings 33. The cylindrical rear portion, in the section not inserted into the intermediate portion, is covered by a sleeve 34 which is firmly attached thereto and is provided with a screwed-in cover 35, permitting access to, and exchange of, a light bulb 40. The front ends of water duct 4 and air duct 5 are not visible since they are hidden by the light bulb 40; the water duct conveys water to a small nozzle which ejects a jet onto the burr 32 in order to cool the drilled area in the tooth. The air duct terminates in one or more nozzles tangentially arranged in respect of the turbine wheel, again in a known manner, and the spent air is ejected towards the burr through small openings in the drill.

The light bulb 40 is obliquely positioned in a suitable bore so as to direct its light towards the tip of the burr; its circumferential shell serves as one of its terminals and is in conductive contact with the material of the front part, while its rear terminal is in conductive contact with the cover 35 in the sleeve 34. The conductor wire 21 which is inserted into a bore in the front part is conductively connected to the sleeve 34 by means of a metal spring 36, whereby current passes from the front end of the cell 2 to the bulb.

All aluminum parts are anodized and thereby electrically insulated from each other, only those surfaces being left bare which are intended for carrying electric current from one part to the adjacent part.

Current passes from the rear terminal of the cell and the contact piston 6 to the bulb, through the rear part 10 and through the intermediate part 20 to the front part 30, wherein the inside of the bore containing the bulb is non-anodized. Likewise, the respective surfaces of the rear part, the intermediate part, and the front part in firm contact are bare in order to permit the current to flow from one part to the other.

The contact piston 6 is urged away from the rear terminal of the cell by the spring 7, as long as the drill is not energized by compressed air admitted by the dentist, but as soon as air is admitted to the handpiece, the air pressure overcomes the resistance of the spring 7 and presses the piston 6 onto the cell, thereby also intensifying the contact force between its front terminal and the contact piece 8. This movement closes the circuit causing the bulb to light up.

It will be understood that the embodiment of the drill handpiece shown in the drawing represents only one of the possible ways of realizing the invention, and that various modifications may be carried out by a person skilled in the art within the scope of the appended claims.

The current conductors are not necessarily in the form of the anodized casing parts, and it is instead proposed to use an insulated wire or rod as conductor between the contact piston (6) to one of the bulb terminals, similarly as shown with regard to the front contact piece. The insulated wire can be readily guided through the channel or groove (17) and through the hollow intermediate part to the electric bulb or other light source. In a similar manner, the conductor (21), instead of being conductively connected to the sleeve (34) and cover (35) by means of the spring (36), may be continued through a suitable bore in the front part (30) to a metal terminal in direct contact with the rear end of the bulb.

In this case the casing may be manufactured from a plastic material by injection moulding, wherein only the contacts to the bulb and the electrical cell would be in the form of metal inserts. This method would, of course, permit the forming of the handpiece in one unit, instead of in three subsequently assembled parts.

It will also be understood that instead of the light bulb another kind of light source may be employed such as a light emitting diode or another light emitting device.

It is also proposed to replace the pneumatically operated switch by a hand-operated switch positioned in the front part of the handpiece. Although this switch would require an additional action of the dentist, it would enable him to light the area to be drilled, even before starting the actual drilling operation.

It may also be advantageous, especially with a casing formed of a plastic material, to replace the air- and water-tubes by drilled bores in the casing material, or to have the ducts partly in the form of drilled bores and partly in the form of tubes.

I claim:

1. Illuminating means for a high-speed drill handpiece, said handpiece comprising an oblong casing in the shape of a cylindrical rear part and a front part, an air-propelled turbine wheel positioned in said front part adapted to drive a burr directly connected to said turbine wheel, and air- and water-duct means, extending from said rear part to said front part, said illuminating means comprising: a light source positioned in said front part in a position effecting light rays to be directed towards the tip of said burr; an electric cell exchangeably placed in a chamber in the cylindrical rear part of said casing, said chamber being positioned eccentrically to the axis of said rear part and being openable through the cylindrical periphery of said rear part, permitting sideways insertion and removal of said electric cell; a first contact point mounted in the rear of said chamber adapted to contact the rear terminal of said electric cell and conductively connected to a first bulb terminal; a second contact point firmly fixed in the front of said chamber and adapted to contact the front terminal of said cell and conductively connected to a second bulb terminal; and switching means adapted to energize or de-energize said light source.

2. The illuminating means of claim 1, comprising a cylindrical sleeve movable along said casing rear part and adapted to respectively cover or uncover said chamber containing said electric cell.

3. The illuminating means of claim 1, wherein said first contact point serves as said switching means in the form of an axially movable piston adapted to be urged in forward direction by pressure of air admitted to said drill to effect contact with said rear terminal of said electric cell, and to be urged in rearward direction by spring means to effect breaking of said contact.

4. The illuminating means of claim 3, wherein said first contact point is in the shape of a stepped piston adapted to be alternatively urged away from said electric cell in rearward direction by a helical spring, and to be urged towards said cell by air presure acting on its rear face.

5. The illuminating means of claim 1, wherein said casing is composed of a substantially cylindrical rear part, an angled, hollow intermediate part, and a front part containing said turbine wheel, said burr and said light source, said three parts being firmly and conductivly connected.

6. The illuminating means of claim 5, wherein said rear part contains said cell chamber of semicircular cross section, open towards the periphery of said cylindrical rear part, and wherein said rear part is recessed to form an internal, longitudinal channel opposite the open portion of said cell chamber.

7. The illuminating means of claim 6, wherein said air- and water-ducts are in the form of tubes communicating with the respective air and water inlet pipes at the rear end of said casing and extending towards the front of said casing inside said longitudinal channel and through the hollow portion of said intermediate part.

8. The illuminating means of claim 1, wherein said light source is an incandescent light bulb.

9. The illuminating means of claim 8, wherein electrical connection between said first contact point and the circumference of said light bulb is formed by the anodized aluminum parts of said casing, said parts being conductively connected through bare, non-anodized surface sections in mutual contact.

10. The illuminating means of claim 8, wherein said second contact point is conductively connected to the rear terminal of said light bulb by means of a wire conductor extending through the hollow portion of said intermediate part and by means of a helical spring extending between the front end of said wire conductor and a metal sleeve covering a portion of said front part and contacting said bulb with a bare portion of its surface.

11. The illuminating means of claim 1, wherein said air- and water-duct means are in the form of bores provided in the material of the casing.

* * * * *